US009937070B2

(12) United States Patent
Skelton et al.

(10) Patent No.: US 9,937,070 B2
(45) Date of Patent: Apr. 10, 2018

(54) DELIVERY DEVICE HANDLE ASSEMBLY FOR THE SEQUENTIAL DEPLOYMENT OF A PROSTHESIS

(71) Applicant: Cook Medical Technologies LLC, Bloomington, IN (US)

(72) Inventors: Eugene E. Skelton, Dublin (IE); Anthony Wright, Dublin (IE); Blayne A. Roeder, Bloomington, IN (US); Edwin E. Macatangay, Bloomington, IN (US); Michael P. DeBruyne, Bloomington, IN (US); Siddharth Vad, Bloomington, IN (US); Natalie Jones, Bloomington, IN (US); Wen Hong Neoh, Bloomington, IN (US); Erik Hughes, Greenwood, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 304 days.

(21) Appl. No.: 14/958,292

(22) Filed: Dec. 3, 2015

(65) Prior Publication Data
US 2016/0158050 A1 Jun. 9, 2016

Related U.S. Application Data

(60) Provisional application No. 62/087,457, filed on Dec. 4, 2014.

(51) Int. Cl.
*A61F 2/966* (2013.01)
*A61F 2/962* (2013.01)
(Continued)

(52) U.S. Cl.
CPC .............. *A61F 2/966* (2013.01); *A61F 2/962* (2013.01); *A61F 2/07* (2013.01); *A61F 2/82* (2013.01);
(Continued)

(58) Field of Classification Search
CPC .. A61F 2/95; A61F 2/954; A61F 2/962; A61F 2/966; A61F 2/97;
(Continued)

(56) References Cited

U.S. PATENT DOCUMENTS 5,776,142 A 7/1998 Gunderson
6,013,020 A 1/2000 Meloul et al.
(Continued)

FOREIGN PATENT DOCUMENTS

EP 2522315 A1 11/2012
WO WO 2011/126690 A1 10/2011
WO WO 2012/036741 A2 3/2012

OTHER PUBLICATIONS

Examination Report for corresponding EP 15275220, dated Sep. 20, 2016, 4 pages.
(Continued)

*Primary Examiner* — Ryan J Severson
(74) *Attorney, Agent, or Firm* — Brinks Gilson & Lione

(57) ABSTRACT

A prosthesis delivery device and method of using the same is described. The delivery device comprises a rotatable inner cannula extending from a proximal end to a distal end with a prosthesis releasably coupled to the proximal end. A delivery handle assembly is disposed at the distal end of the delivery device. The handle comprises a first handle disposed about the inner cannula, a rotary dial rotatably disposed about a distal end of the first handle and a second handle disposed about at least a portion of the distal end of the first handle. The second handle is longitudinally moveable relative to the first handle between a first position wherein the sheath is coaxially disposed about the prosthesis and rotation of the rotary dial is prevented, and a second
(Continued)

position wherein the sheath is retracted distally to expose at least a portion of the prosthesis and rotation of the dial is permitted.

16 Claims, 12 Drawing Sheets

(51) Int. Cl.
  *A61F 2/82* (2013.01)
  *A61F 2/95* (2013.01)
  *A61F 2/07* (2013.01)

(52) U.S. Cl.
  CPC ............ *A61F 2002/9517* (2013.01); *A61F 2002/9534* (2013.01); *A61F 2002/9665* (2013.01)

(58) Field of Classification Search
  CPC ...... A61F 2002/9505; A61F 2002/9511; A61F 2002/9517; A61F 2002/9665
  See application file for complete search history.

(56) References Cited

U.S. PATENT DOCUMENTS

| | | | | |
|---|---|---|---|---|
| 7,066,951 B2* | 6/2006 | Chobotov | ............... | A61F 2/07 623/1.12 |
| 7,338,518 B2* | 3/2008 | Chobotov | ............... | A61F 2/07 623/1.11 |
| 7,356,903 B2* | 4/2008 | Krivoruchko | ............ | A61F 2/95 29/272 |
| 7,381,216 B2 | 6/2008 | Buzzard et al. | | |
| 7,935,141 B2* | 5/2011 | Randall | ............... | A61F 2/95 606/108 |
| 7,976,574 B2* | 7/2011 | Papp | ............... | A61F 2/95 623/1.11 |
| 8,083,752 B2* | 12/2011 | Bolduc | ............... | A61B 17/064 606/108 |
| 8,262,718 B2 | 9/2012 | Chuter et al. | | |
| 8,303,546 B2 | 11/2012 | Cordeiro et al. | | |
| 8,475,514 B2 | 7/2013 | Hartley et al. | | |
| 8,585,750 B2* | 11/2013 | Argentine | ............... | A61F 2/95 623/1.12 |
| 8,808,346 B2* | 8/2014 | Jimenez, Jr. | ............... | A61F 2/95 623/1.11 |
| 8,858,610 B2* | 10/2014 | Brown | ............... | A61F 2/95 604/500 |
| 8,968,380 B2* | 3/2015 | Nimgaard | ............... | A61F 2/95 604/159 |
| 9,144,510 B2* | 9/2015 | Havel | ............... | A61F 2/95 |
| 9,173,756 B2* | 11/2015 | Hopkins | ............... | A61F 2/95 |
| 9,320,589 B2* | 4/2016 | Bolduc | ............... | A61B 17/064 |
| 9,326,872 B2* | 5/2016 | Sokel | ............... | A61F 2/95 |
| 9,364,355 B2* | 6/2016 | Hopkins | ............... | A61F 2/95 |
| 9,675,486 B2* | 6/2017 | Jimenez, Jr. | ............... | A61F 2/95 |
| 2004/0138734 A1 | 7/2004 | Chobotov et al. | | |
| 2005/0027306 A1 | 2/2005 | Krivoruchko et al. | | |
| 2005/0154443 A1 | 7/2005 | Linder et al. | | |
| 2005/0273151 A1 | 12/2005 | Fulkerson et al. | | |
| 2010/0211052 A1* | 8/2010 | Brown | ............... | A61F 2/95 606/1 |
| 2010/0274227 A1 | 10/2010 | Khairkhahan et al. | | |
| 2011/0251664 A1* | 10/2011 | Acosta De Acevedo | . | A61F 2/07 623/1.11 |
| 2011/0257719 A1 | 10/2011 | Argentine | | |
| 2011/0288558 A1 | 11/2011 | Nimgaard | | |
| 2012/0046652 A1 | 2/2012 | Sokel | | |
| 2013/0013049 A1 | 1/2013 | Melsheiner et al. | | |
| 2013/0131774 A1* | 5/2013 | Nabulsi | ............... | A61F 2/95 623/1.11 |
| 2013/0338787 A1 | 12/2013 | Hopkins et al. | | |
| 2013/0338788 A1* | 12/2013 | Hopkins | ............... | A61F 2/95 623/23.7 |
| 2016/0015542 A1* | 1/2016 | Hopkins | ............... | A61F 2/95 623/1.12 |

OTHER PUBLICATIONS

Chuter, Timothy A. et al., "Modular branched stent graft for endovascular repair of aortic arch aneurysm and dissection", Journal of Vascular Surgery, Oct. 2003, pp. 859-863.
European Search Report for corresponding EP 15275220, dated Apr. 22, 2016, 8 pages.
European Search Report for EP Application No. 17192738 dated Dec. 6, 2017, 4 pages.

* cited by examiner

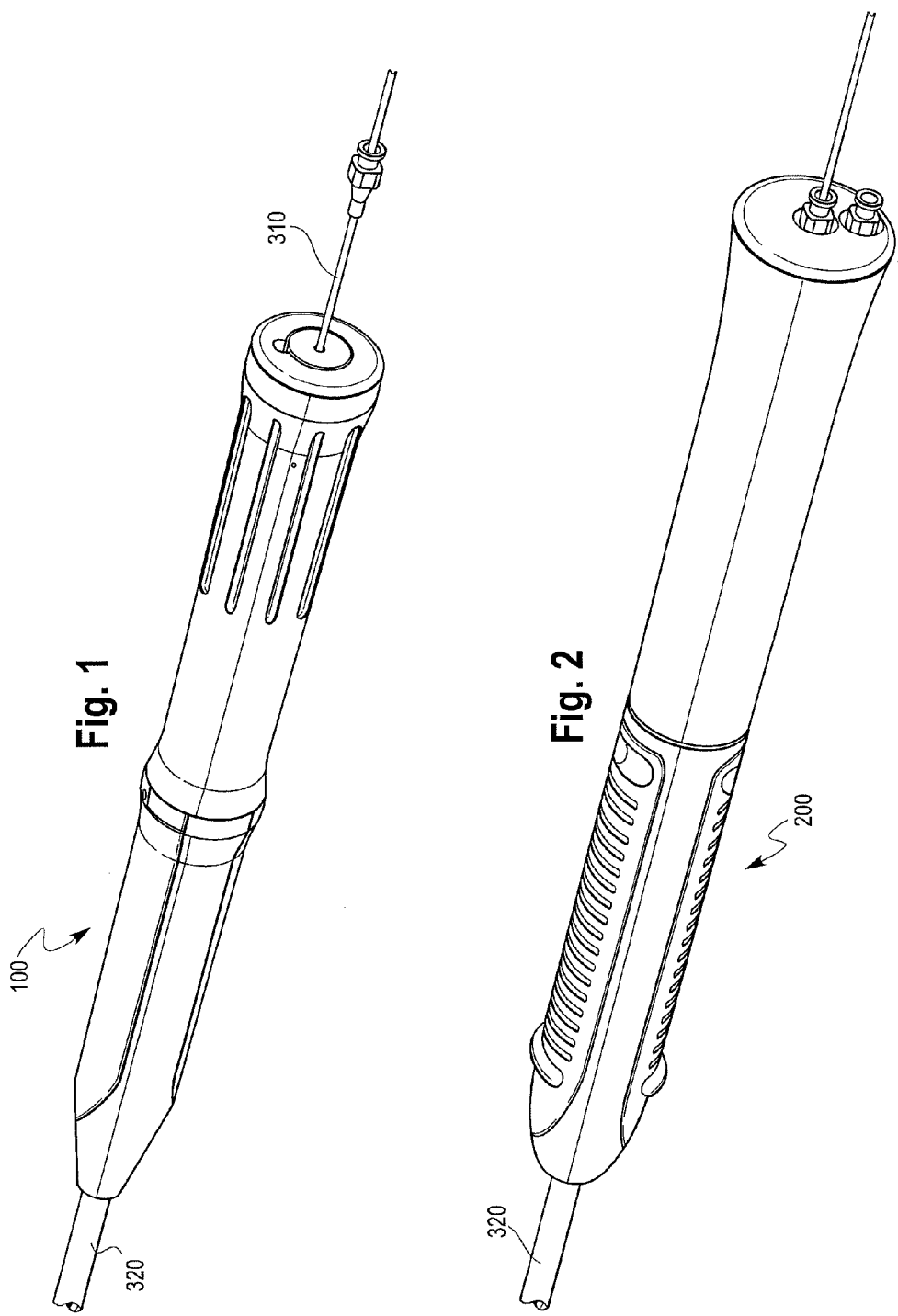

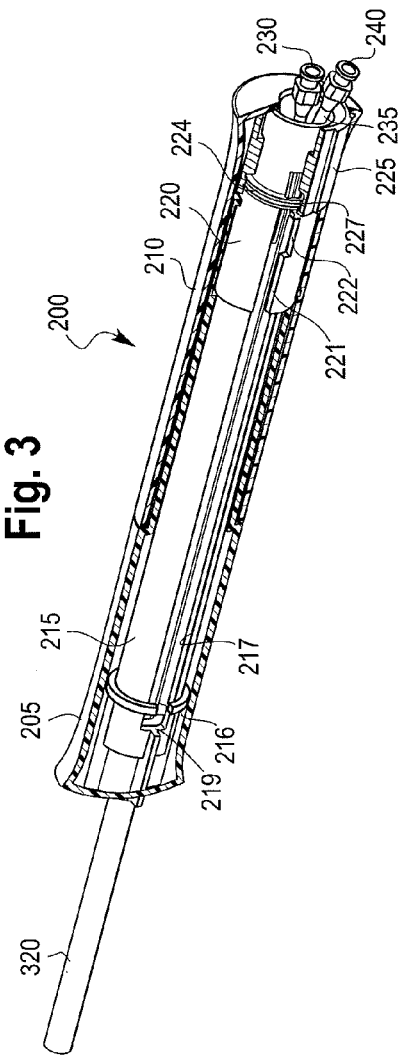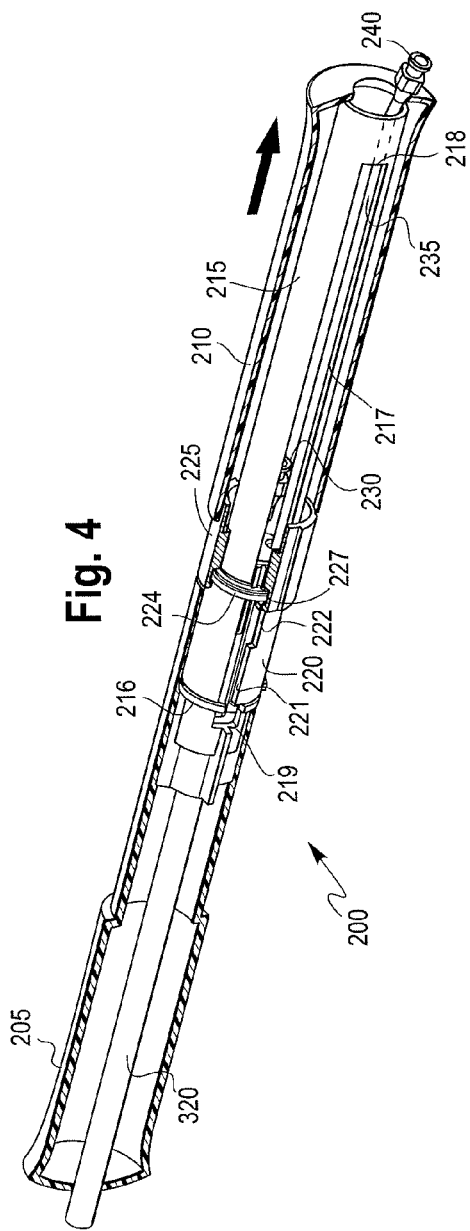

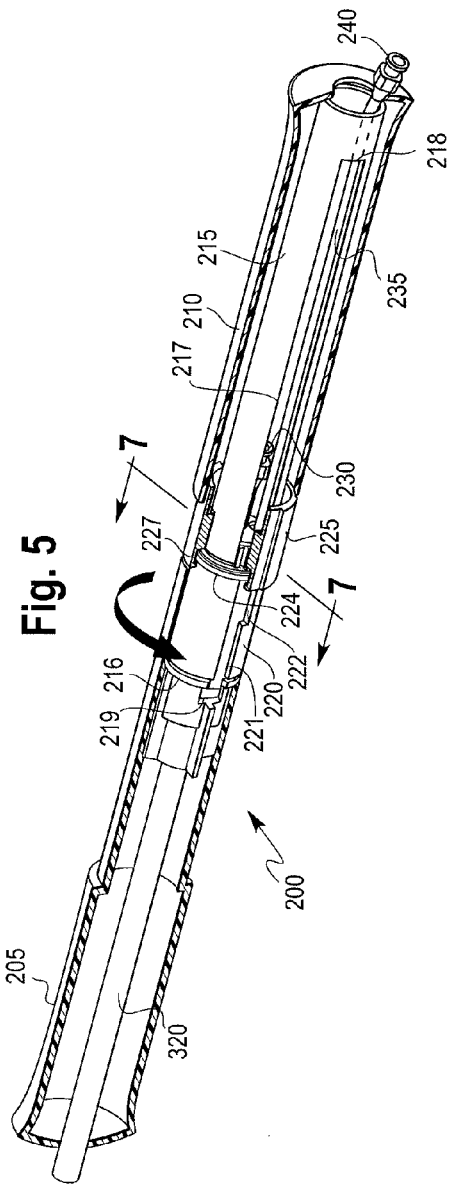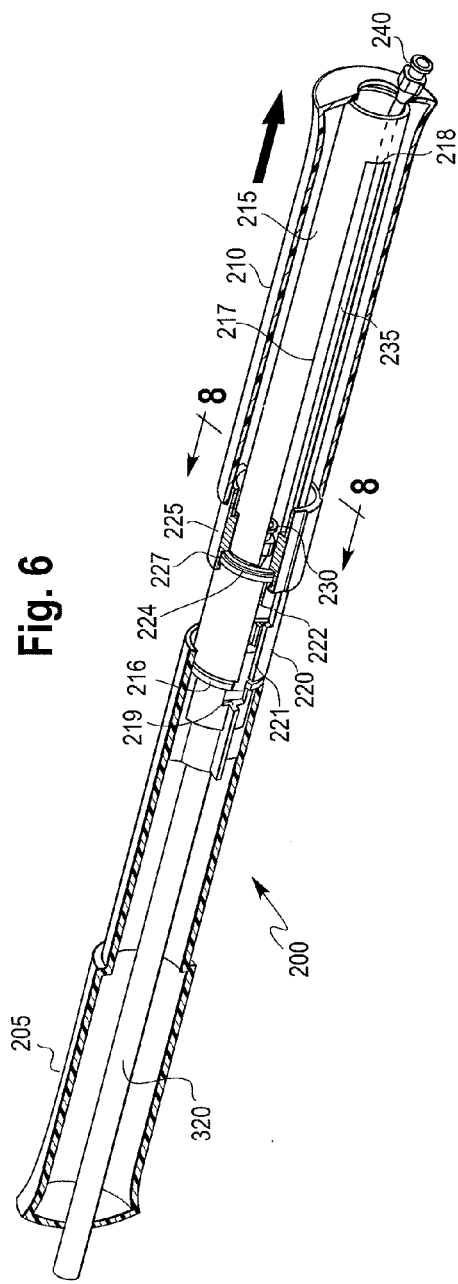

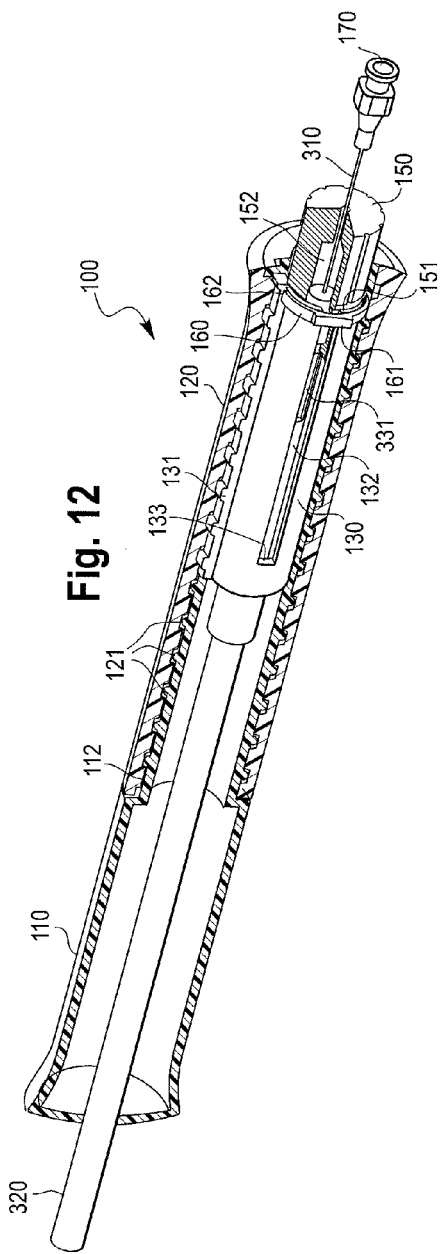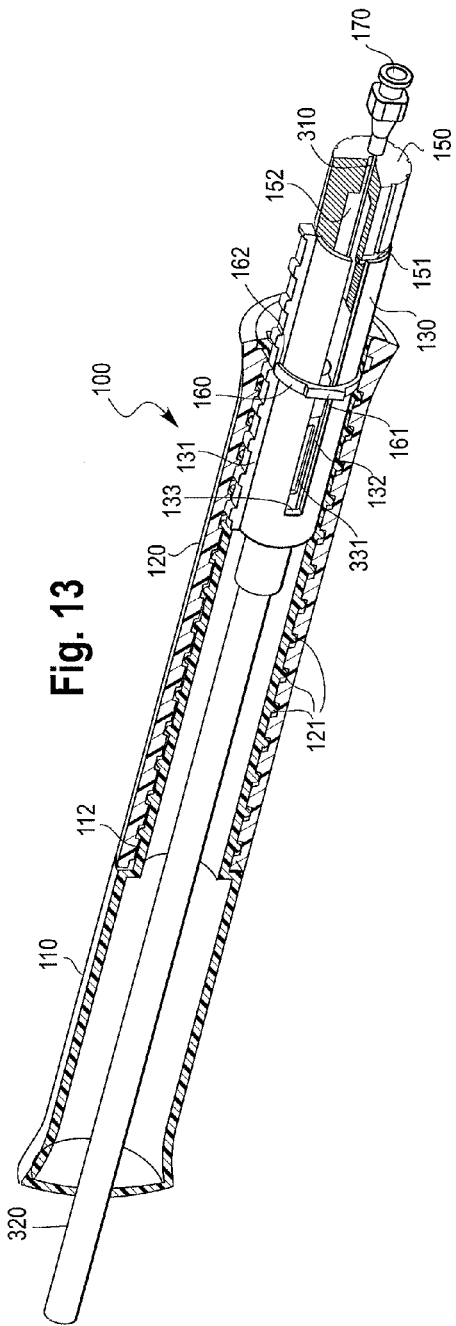

DELIVERY DEVICE HANDLE ASSEMBLY FOR THE SEQUENTIAL DEPLOYMENT OF A PROSTHESIS

RELATED APPLICATIONS

The present application claims the benefit of the filing date under 35 U.S.C. § 119(e) of Provisional U.S. Patent Application Ser. No. 62/087,457 filed Dec. 4, 2014, which is hereby incorporated by reference.

BACKGROUND

The present invention relates to delivery devices for prostheses, such as stents, grafts and stent grafts (collectively prostheses) in the vascular system of a patient. In particular, the invention relates to a delivery device having a handle that permits controlled and sequential release and deployment of a prosthesis from the delivery device.

SUMMARY

A prosthesis delivery device is disclosed. The delivery device comprises a proximal end and a distal end and a rotatable inner cannula extending from the proximal end to the distal end. A prosthesis is releasably coupled to the proximal end of the inner cannula and a sheath is coaxial with the inner cannula and extends at least partially between the proximal and distal ends of the inner cannula. A delivery handle assembly is located at the distal end of the delivery device. In one example, the delivery handle assembly comprises a first or front handle disposed about the inner cannula, wherein the first handle comprises a rotary dial rotatably disposed about a distal end thereof and a second handle disposed about at least a portion of the distal end of the first handle, wherein the second handle is longitudinally moveable relative to the first handle between a first position and a second position. When the second handle is in the first position, the sheath is coaxially disposed about the prosthesis and rotation of the dial is prevented, and when the second handle is in the second position, the sheath is retracted distally to expose at least a portion of the prosthesis and rotation of the dial is permitted.

In one example, second handle slides distally from the first position to the second position. In another example, the second handle is axially rotated distally to move the second handle from the first position to the second position.

In another example, a method for sequentially releasing a prosthesis from a delivery device is disclosed. The method comprises the steps of actuating the second handle from a first position to a second position to retract the sheath to expose at least a portion of the prosthesis, rotating the rotary dial to release the proximal end of the prosthesis and actuating the second handle from a second position to a third position to release a distal end of the prosthesis.

DESCRIPTION OF THE DRAWINGS

FIG. 1 is a rear perspective view of one example of a handle assembly of a prosthesis delivery device.

FIG. 2 is a rear perspective view of another example of a handle assembly of a prosthesis delivery device.

FIG. 3 is a partial sectional view of the prosthesis delivery device of FIG. 2.

FIG. 4 is a partial sectional view of the prosthesis delivery device of FIG. 2 during deployment of a prosthesis.

FIG. 5 is a partial sectional view of the prosthesis delivery device of FIG. 2 during deployment of a prosthesis.

FIG. 6 is a partial sectional view of the prosthesis delivery device of FIG. 2 during deployment of a prosthesis.

FIG. 12 is a partial sectional view of the prosthesis delivery device of FIG. 1 during deployment of a prosthesis.

FIG. 13 is a partial sectional view of the prosthesis delivery device of FIG. 1 during deployment of a prosthesis.

DETAILED DESCRIPTION

Figure 8:
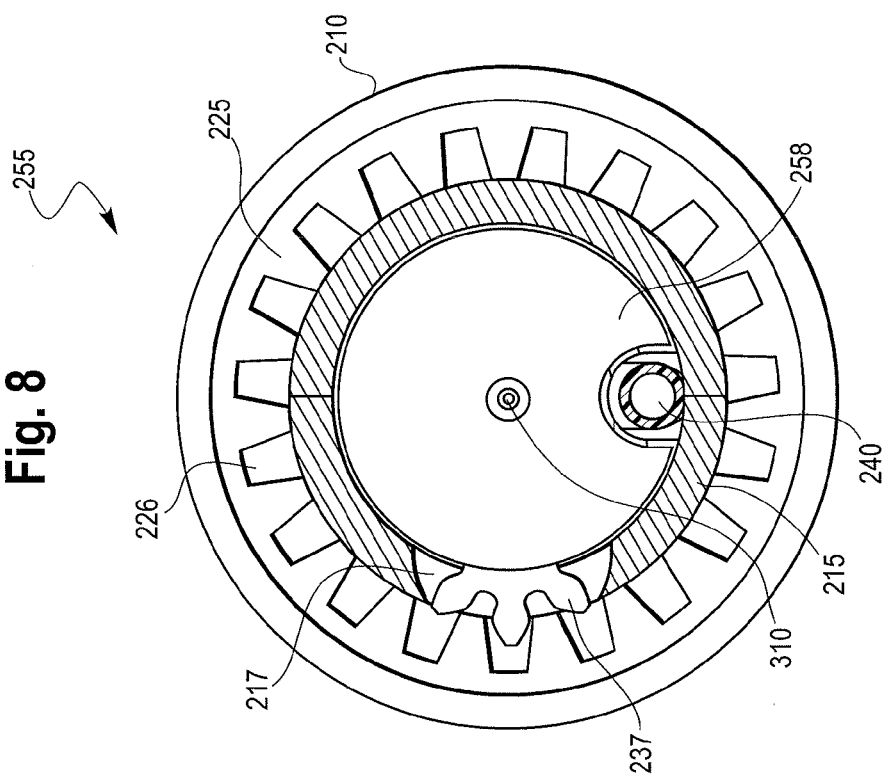
FIG. 8 is a cross-sectional view of the gear system in the handle of the delivery device of FIG. 2 at another stage of deployment of a prosthesis.

The embodiments described in this disclosure will be discussed generally in relation to deployment of prostheses, such as stents, grafts and stent grafts into the aorta, but the disclosure is not so limited and may be applied to other areas of the vasculature or other body vessels or lumens.

In the present application, the term "proximal" refers to a direction that is generally closest to the heart during a medical procedure, while the term "distal" refers to a direction that is furthest from the heart during a medical procedure.

The term "stent graft" refers to a device that has a tubular body of biocompatible graft material and at least one stent fastened to the tubular body to define a lumen through the stent graft. The stent graft may be bifurcated and/or may include fenestrations, side arms, or the like. Other arrangements of stent grafts also are within the scope of this disclosure.

The delivery device described herein facilitates the delivery and deployment of a prosthesis at an implantation site within a body vessel. The handle assembly preferably comprises mechanisms to prevent a physician from performing deployment steps out of sequence while helping to ensure that all deployment steps are completed. Particularly, the handle assembly is designed to allow the physician the ability to perform only one deployment step at a time, and until one step is completed, the next deployment step cannot be initiated and/or performed.

In one non-limiting example, the handle assembly may be configured to facilitate deployment of a bifurcated stent graft in the aorta in a preferred sequence including partial sheath withdrawal to expose the proximal stent and contralateral stent limb, followed by deployment of the proximal stent, further sheath withdrawal to expose the ipsilateral limb and finally trigger wire release to facilitate deployment of the distal end of the stent graft.

One example of a deployment handle that may be used with a delivery device for the controlled and sequential deployment of a stent graft is illustrated in FIGS. 2-9, identified herein as a "pull-back" deployment handle assembly 200. An alternative example of a deployment handle assembly is illustrated in FIGS. 1, 10-14, identified herein as a "rotational" deployment handle assembly 100.

The pull-back deployment handle assembly 200 is located at the distal end of the device and is intended to remain outside of the patient during a procedure. The handle is actuated by the physician to release a prosthesis from the proximal end 600 of the delivery device. Any portion of the handle and its various components may be provided with gripping features that provide secure and/or ergonomic gripping by the physician and provide the physician with tactile feedback while gripping and/or operating the handle.

FIGS. 2-9 illustrate the pull back deployment handle assembly 200 as it is operated by a user to sequentially release the proximal and distal ends of a prosthesis, such as a stent graft. In operation, the first handle 205 is a stationary proximal handle that allows the physician to grip and stabilize the delivery device. The second handle 210 is distal to the first handle and is actuated by the physician during deployment of the prosthesis.

Figure 9:
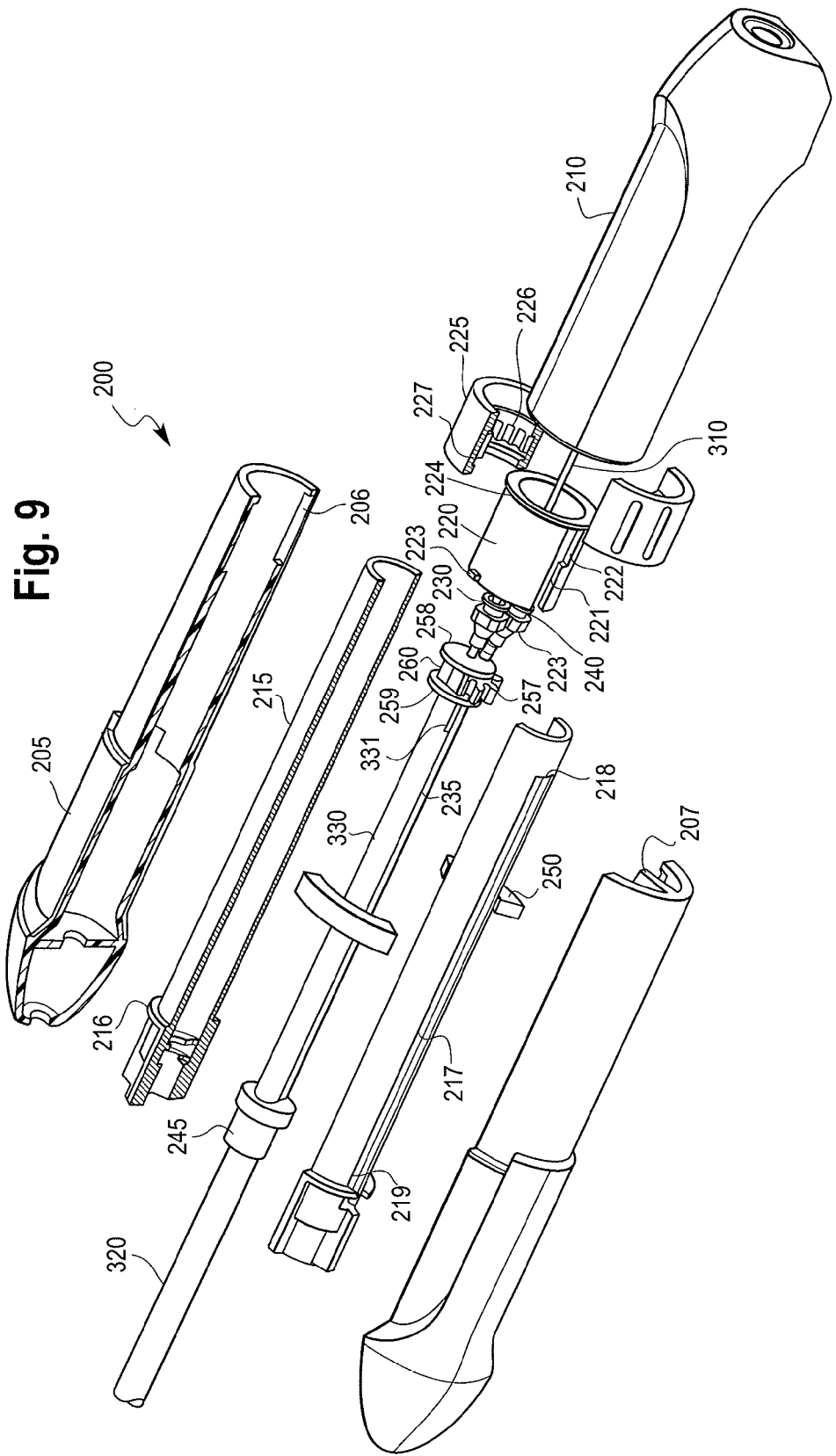
FIG. 9 is an exploded view of a prosthesis delivery device of FIG. 2.

The pull back deployment handle assembly 200 further includes a locking mechanism 250 that is shown in FIG. 9. This locking mechanism 250 is disposed about the surface of the first handle 205 and prevents unintended or premature movement of the second handle 210 relative to the first handle 205. The locking mechanism 250 may engage the first handle 205 through latching or other engagement, including, but not limited to a pin, a clip and the like.

As illustrated in FIG. 3, the first handle 205 is disposed at the proximal end of handle assembly 200 and about the distal end of a sheath 320. The first handle 205 extends the length of the deployment handle assembly 200 and defines a generally tubular interior space that houses other components of the handle assembly. The second handle 210 is partially disposed about the distal end of the first handle 205. When the second handle 210 is pulled distally from a first position (FIG. 3) to a second position (FIG. 4) the sheath 320 is at least partially withdrawn to expose a proximal portion of the prosthesis carried at the proximal end 600 of the device and, after the proximal end of the prosthesis is released, further pull back of the second handle 210 (FIG. 6) to a third position further withdraw the sheath 320 to release the distal end of the prosthesis.

To accomplish this, the second handle 210 is engageable with the distal end of a handle rear inner 215 such that retraction of the second handle 210 in a distal direction also retracts the handle rear inner 215 relative to the first handle 205. As shown in FIG. 3, the handle rear inner 215 is initially positioned within the first handle 205 and is distally slidable relative to the first handle 205. The proximal end of the handle rear inner 215 is attached to the sheath 320 at the sheath connector 245. The handle rear inner 215 has a body slot 217 that extends along one side of the handle rear inner 215. The body slot 217 provides a track for a tab 207 that protrudes from an inner surface of the first handle 205 and prevents rotational movement of the handle rear inner 215. The proximal end 219 of the slot 217 limits the distal-most position of the handle rear inner 215 while the distal end 218 of the slot 217 limits the proximal most position of the handle rear inner 215. The handle rear inner 215 further includes a proximal lip 216 that limits the distal movement of the handle rear inner 215 and the attached second handle 210 when the proximal lip 216 encounters and/or abuts the proximal end of the rotary dial 220. Distal movement of the handle rear inner 215 is restricted until, as discussed below, the rotary collar 225 is fully rotated.

The rotary collar 225 is disposed about the handle rear inner 215. The proximal end of the rotary collar 225 can rotate about the distal end of the rotary dial 220. Specifically, as shown in FIG. 4, threading 224 of the rotary dial 220 engages the collar threading 227 located at the proximal end of the rotary collar 225. When the rotary collar 225 is rotated, gear engaging teeth 226 on the inside surface of the rotary collar 225 engage with rotation gears 255 to rotate the inner cannula 310 to release the proximal end of the prosthesis.

The rotary dial 220 serves to limit the movement of the handle rear inner 215 and prevent the continued withdrawal of the sheath 320 until the rotary collar 225 has been fully rotated. The rotary dial 220 is, as noted above, located proximal to the rotary collar 225 and is also disposed about the handle rear inner 215. The rotary dial 220 includes a movement slot 221 and an engagement slot 222. The movement slot 221 extends from the proximal end of the rotary dial 220 and allows the rotary dial 220 to receive the tab 207 protruding from the inner surface of the first handle 205. The engagement slot 222 is located at the distal end of the rotary dial 220 and serves to lock the rotary dial 220 in place when tab 207 is rotated to fit into and engage slot 222. The inner cannula 310 extends from the distal end of the handle assembly 200 to the proximal end 600 of the delivery device. A guide wire flush port 230 is located at the distal end of the inner cannula 310 and provides access to the guide wire flush tube (not shown) that is disposed about the cannula 310 and is connected to the positioner 330.

As shown in FIG. 9, the positioner 330 is disposed about the inner cannula 310 and extends proximally from the rotation gears. The sheath 320 is at least partially disposed about the positioner 330 and is distally moveable relative to the positioner 330. The positioner 330 includes an attachment slot 331 that is configured to receive the tab 207 to retain the positioner 330 in a stationary position.

The sheath 320 extends from the proximal end 600 of the delivery device to the proximal end of the first handle 205. The proximal end of the handle rear inner 215 is attached to the distal end of the sheath 320 at sheath connector 245. The sheath connector 245 provides access to the sheath 320 for the positioner 330 and the sheath flush tube 235. The sheath flush tube 235 connects the sheath flush port 240 to the sheath connector 245. The sheath flush port 240 is flushed with saline when the delivery device is introduced into the patient's body.

Figure 7:
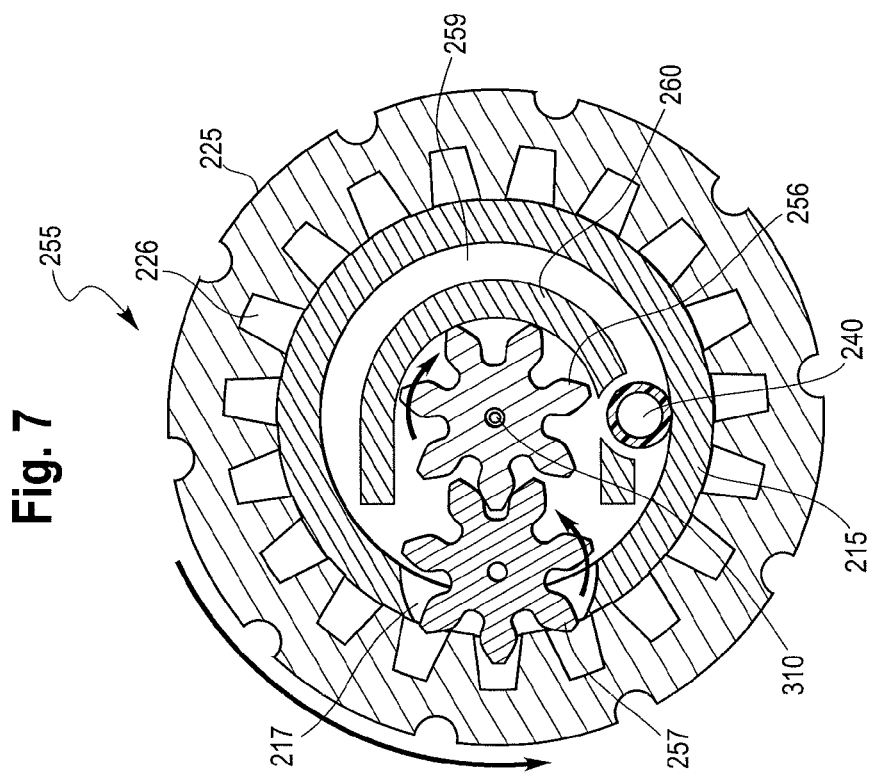
FIG. 7 is a cross-sectional view of the gear system in the handle of the delivery device of FIG. 2 at one stage of deployment of a prosthesis.

The rotation gears 255 facilitate rotation of the inner cannula 310 through rotation of the rotary collar 225. As shown in FIG. 9, the rotation gears 255 are attached to the distal end of the positioner 330. A cross section of the rotation gears 255 is shown in FIGS. 7-8. The rotation gears 255 include a first gear 256 and a second gear 257. The rotation gears 255 are retained between two disks: a proximal disk 259 is attached to the base of the positioner 330 and a distal disk 258 forms the distal end of the rotation gears 255. The proximal disk 259 and the distal disk 258 have openings that accommodate the inner cannula 310 and the sheath flush port 240. A rotation gear retention slot 260 extends between the proximal disk 259 and distal disk 258 to form a slot for the retention of the first gear 256. The first gear 256 is disposed about and is attached to the inner cannula 310. The second gear 257 is contained between the slot 217 of the handle rear inner 215 and the teeth of the first gear 256. As will be described in more detail below, the gear engaging teeth 226 of the rotary collar 225 engage the teeth of the second gear 257 to cause rotation of the second gear 257 in a first direction. The second gear 257 interacts with the teeth of the first gear 256 to cause the first gear 256 to rotate, thus imparting rotation to the inner cannula.

One example of a delivery and deployment sequence using a delivery device with deployment handle assembly 200 is described below.

A delivery device may be initially flushed with saline through the flush port 240. A guide wire may then be introduced into the device though the distal end, allowing the device to be introduced into a patient's vasculature and tracked to a desired location. FIG. 3 shows the deployment handle assembly 200 after the delivery device has been introduced into the patient's body and before any deployment steps have been performed. At this time, any locking mechanism and/or safety latch 250 or other mechanism can be operated to "unlock" the handle assembly 200 to allow the handle assembly to be operated and a prosthesis deployment sequence to commence.

Next, the second handle 210 is pulled back in a distal direction along the outer surface of the first handle 205 as indicated by the arrow shown in FIG. 4. In operation, the physician places one hand (e.g., a "non-dominant" hand) on the front or first handle 205 and a second hand (e.g., a "dominant" hand) on the rear or second handle 210. The physician slowly pulls the second handle 210 in the distal direction with one hand as indicated by the arrow in FIG. 4, while the other hand gripping the first handle 205 stabilizes the device. Pulling back on the second handle 210 causes the attached sheath 320 to also retract in a distal direction, thereby unsheathing at least a proximal portion of the prosthesis carried at the proximal end 600 of the delivery device. The positioner 330 preferably has sufficient rigidity and/or stiffness to resist buckling as the sheath 320 is retracted distally over it. The handle rear inner 215 moves distally as the second handle 210 is pulled back until the proximal lip 216 on the handle rear inner 215 hits the proximal end of the rotary dial 220, which prevents further distal movement of the handle rear inner 215 at this stage of deployment. This prevents the premature release of the distal attachment of the prosthesis. When the proximal lip 216 encounters the proximal end of the rotary dial 220, the second handle 210 is pulled back a sufficient distance to expose the rotary collar 225 as shown in FIG. 4.

Figure 20:
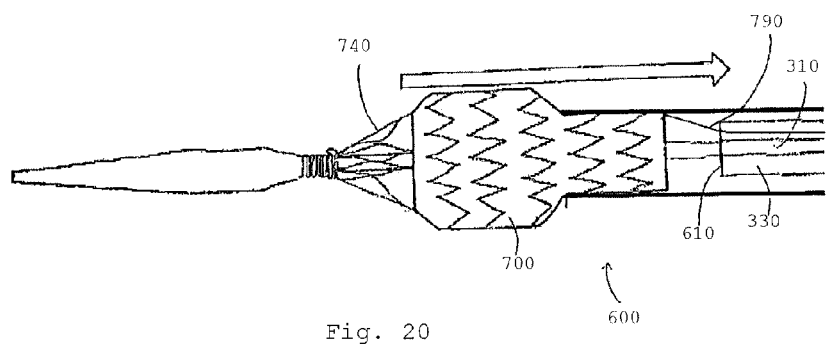

As shown in FIG. 5, the rotary collar 225 is now accessible to the physician and can be manually rotated. As previously mentioned, rotation of the rotary collar 225 imparts rotation to the rotation gears 255 as illustrated in FIG. 7. As described above, the gear engaging teeth 226 of the rotary collar 225 engage with the teeth of the second gear 257 to cause the second gear 257 to turn in a counter-clockwise direction as the rotary collar 225 is rotated in a counter-clockwise direction. The second gear 257 then interacts with the gears of the first gear 256, causing the first gear 256 to rotate in a clockwise direction which imparts rotation to the attached cannula 310. As will be described in connection with FIGS. 20-21, this rotation of the inner cannula 310 releases the proximal end of the prosthesis. Until the rotary collar 225 is rotated to release the proximal end of the prosthesis, the physician cannot further pull back the second handle 210 to release of the distal end of the prosthesis, thus preventing the various steps of deployment from being performed out of a preferred sequence.

As illustrated in FIG. 6, the collar threading 227 located at the proximal end of the rotary collar 225 is disposed about the dial threading 224 located at the distal end of the rotary dial 220. As the rotary collar 225 is rotated, the collar threading 227 and the dial threading 224 are engaged. The respective threading 227, 224 permits a selected number of rotations of the rotary collar 225 around the rotary dial 220 while the rotary dial 220 remains stationary. The selected number of rotations imparted to the rotary collar 225 is preferably the number of rotations required to release the proximal end of the prosthesis. When the rotary collar 225 has been sufficiently rotated about the rotary dial 220 such that release of the proximal end of the prosthesis has been achieved, the rotary collar 225 can then be further rotated (e.g., one additional/final rotation) which imparts rotation to the rotary dial 220. This causes tab 207 to be released from the engagement slot 222 of the rotary dial 220 and move into the slot 221 of the rotary dial 220. In addition, the tab 223 on the proximal end of the rotary dial 220 is rotated into the rotary collar movement slot 206 of the first handle 205. This final rotation of the rotary collar 225 engages the rotary collar 225 with the rotary dial 220 and allows both the rotary collar 225 and the rotary dial 220 to be pulled back in a distal direction with the second handle 210 as shown in FIG. 6.

In other words, the physician can now further pull back the second handle 210 to further retract the sheath 320 in a distal direction as shown by the arrow in FIG. 6. As the second handle 210 is pulled back, it also moves the handle rear inner 215 in a distal direction. The proximal lip 216 of the handle rear inner 215 engages the proximal end of the rotary dial 220 to also move the rotary dial 220 and the rotary collar 225 together in a distal direction. The rotary dial 220 is prevented from being entirely withdrawn out of the first handle 205 because tab 223 protruding from the rotary dial 220 is engaged with movement slot 206 (FIG. 9) formed in the distal end of the first handle 205.

Figure 22:
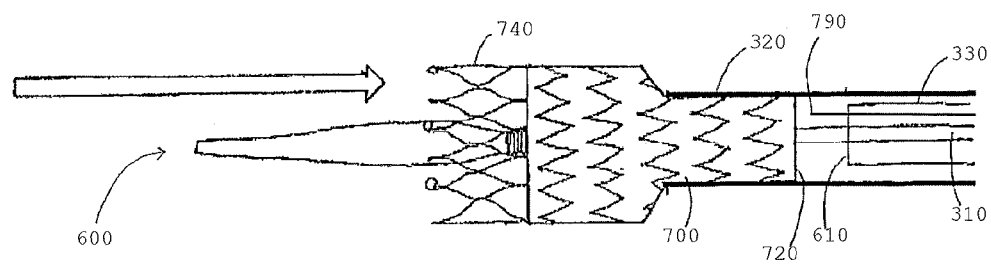
Figure 23:
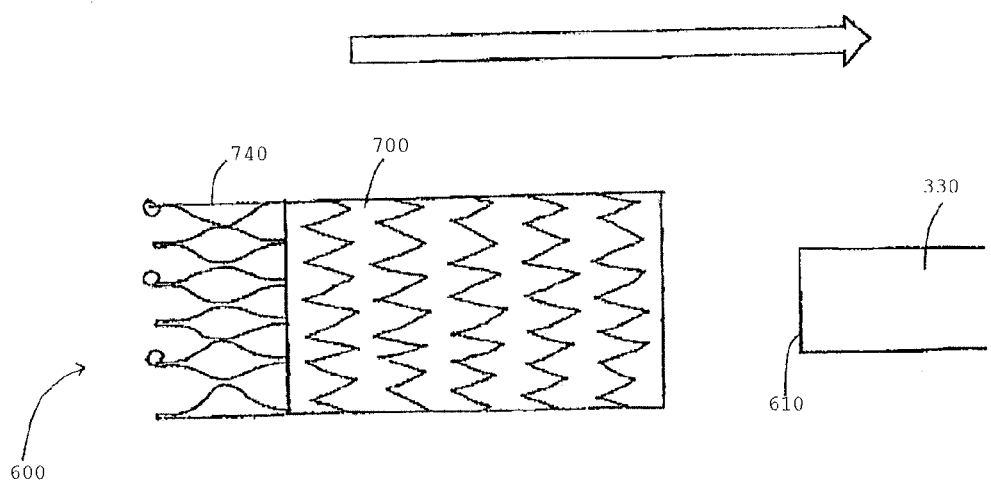

FIGS. 22-23 illustrate the release of the prosthesis as the second handle 210 is further pulled back as shown in FIG. 6. Specifically, pulling back further on the second handle 210 exposes the distal end of the prosthesis. The simultaneous withdrawal of the rotary dial 220 with the second handle 210 withdraws the cannula 310 distally from the body of the prosthesis and the withdrawal of the rotary collar 225 withdraws the trigger wire 790 from the distal end of the prosthesis to thereby release the prosthesis from the delivery device and deploy it within the body at the desired deployment site.

In an alternative example of the handle assembly, FIGS. 1 and 10-14 illustrate the rotational deployment handle assembly 100 as it is operated by a user to release the proximal and distal ends of a prosthesis, such as a stent graft from the delivery device. In one aspect, the rotational deployment handle assembly 100 differs from the pull back handle assembly 200 in that the second handle 120 is moved distally relative to the first handle 110 by axial rotation of the second handle 120.

Figure 14:
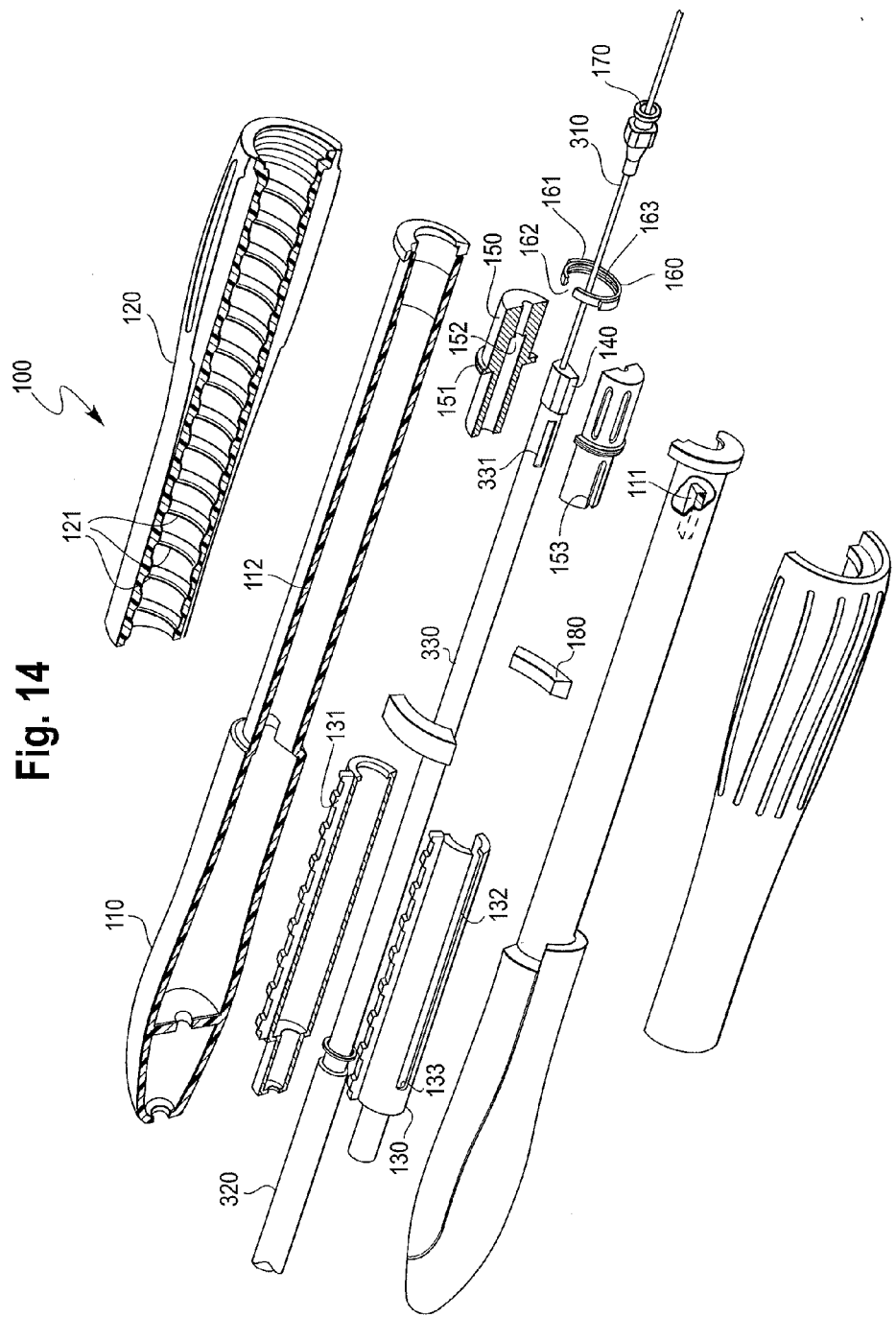
FIG. 14 is an exploded view of the prosthesis delivery device of FIG. 1.

The rotational deployment handle assembly 100 remains outside of the patient during a delivery and deployment procedure. The various components of the handle assembly 100 can be actuated by the physician to release the prosthesis from the proximal end of the delivery device. As shown in FIGS. 10-13, the rotational deployment handle 100 includes a front or first handle 110 and a rear or second handle 120. The handle assembly 100 also preferably includes a locking mechanism 180 that is shown in FIG. 14 which may engage the first handle 110 through a latching or other engagement, such as a pin, clip and others known to one of skill in the art. This locking mechanism 180 is configured to prevent the second handle 120 from rotating relative to the first handle 110, thereby preventing unintended or premature deployment of any portion of the prosthesis.

The first handle 110 provides the physician a consistent point of reference for the prosthesis and allows the physician to grip and stabilize the device during a procedure. The proximal end of the first handle 110 is disposed about the distal end of the sheath 320. The first handle 110 is a generally tubular structure that forms an interior space that serves generally as a housing for various components of the handle assembly 100. The first handle 110 has a slot 112 that allows the teeth 131 of a shuttle 130 to protrude through the surface of the first handle 110. As shown in FIG. 14, a tab 111 protrudes from the inner surface of the distal end of the first handle 110. This tab 111 engages with the distal end of the positioner 330 to keep the positioner 330 stationary as the prosthesis is deployed.

The second handle 120 of the rotational deployment handle assembly 100 is disposed about the distal end of the first handle 110 and is actuated by manual rotation by the user. Specifically, the inner surface of the second handle 120 comprises threading 121 that engages the teeth 131 of the shuttle 130. As will be described more fully below, rotation of the second handle 120 engages the shuttle 130 and advances the shuttle 130 in a distal direction along the positioner 330.

The shuttle 130 is attached at the proximal end 133 to the sheath 320 and is disposed about the positioner 330. As the shuttle 130 moves distally along the positioner 330, it pulls the sheath 320 distally along the positioner 330. The body of the shuttle 130 has a slot 132 that extends longitudinally along one side of the shuttle 130. The slot 132 provides a track for the tab 111 that extends from the inner surface of the first handle 110 and prevents rotational movement of the shuttle 130 as it moves distally along the length of the positioner 330. The proximal end 133 of the shuttle slot 132 limits the distal most position of the shuttle 130.

As shown in FIG. 14, a rotary dial 150 having a distal end and a proximal end 153 is disposed about the distal end of the positioner 330. The rotary dial 150 provides rotational control of the inner cannula 310. A rotary cog 140 is located at the base of the positioner 330 and is attached to the inner cannula 310. The proximal end 153 of the rotary dial 150 forms a slot 152 that is disposed about the rotary cog 140. A slot at the proximal end 153 of the rotary dial 150 engages the tab 111 of the first handle 110 to only allow the rotary dial 150 to move in a distal direction while tab 111 is engaged within the slot 153. Once the rotary dial 150 is moved in a distal direction, the rotary dial 150 is then positioned such that it is disposed about the rotary cog 140 such that rotation of the rotary dial 150 causes the rotary cog 140 (and the connected inner cannula 310) to rotate as well. Further, as will be described below, the distal end of the trigger wire 790 of FIGS. 19-22 is attached to the rotary dial 150, such that distal movement of the rotary dial 150 retracts the trigger wire 790 to release the distal end of the prosthesis.

Figure 11:
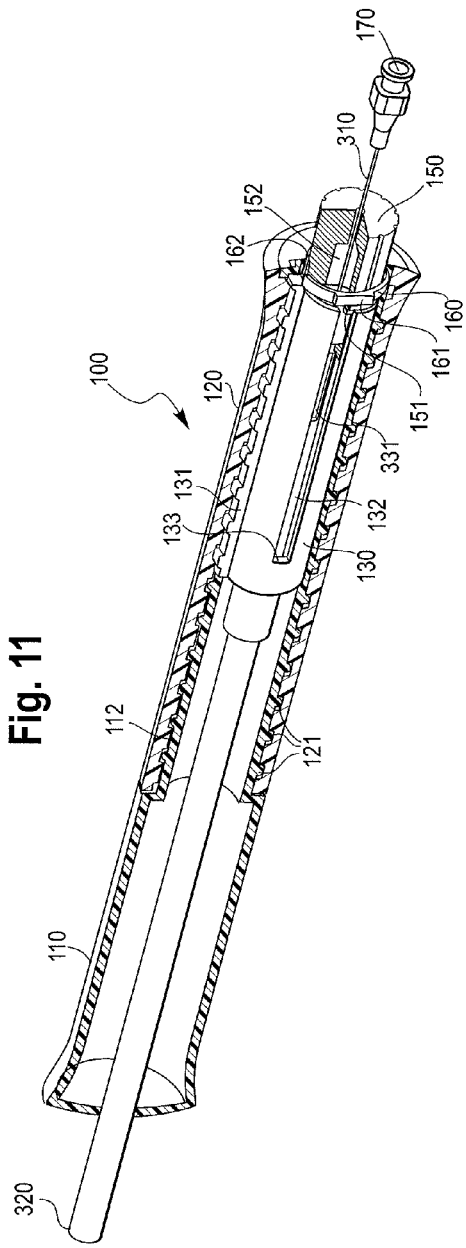
FIG. 11 is a partial sectional view of the prosthesis delivery device of FIG. 1 during deployment of a prosthesis.

As shown in FIGS. 11 and 14, a collar 160 retained within the distal end of the first handle limits the movement of the shuttle 130 by preventing the second handle 120 from rotating before the rotary dial 150 is fully rotated. The collar 160 has a retention tab 161 on either side of the collar 160 that is retained in a slot 112 of the first handle 110 that prevents the collar 160 from rotating. The inner surface of the collar 160 has inside threads 163 that can engage with the rotary dial threading 151 of the rotary dial 150. As will be described more fully below, rotation of the rotary dial 150 engages the rotary dial threading 151 with the inside threads 163 of the collar 160 and advances the collar 160 in a proximal direction. The collar 160 also has a top opening 162 that is sufficiently wide to allow the teeth 131 to move past the collar 160.

The inner cannula 310 extends from the distal end of the rotational deployment handle assembly 100 to the proximal end 600 of the delivery device. The flushing port 170 is located at the distal end of the inner cannula 310 and provides access to the flushing tube (not shown) that is disposed about the inner cannula 310. The flushing tube is attached to the positioner 330 and allows both the inner cannula 310 and the sheath 320 to be flushed with saline as the delivery device is introduced into the body.

The sheath 320 is disposed about the prosthesis that is releasably retained at the proximal end 600 of the delivery device. The sheath extends along the length of the device and is attached to the shuttle 130 at its distal end, such that distal movement of the shuttle 130 causes the sheath 320 to be retracted.

One example of a delivery and deployment sequence using a delivery device with deployment handle assembly 100 is described below.

Figure 10:
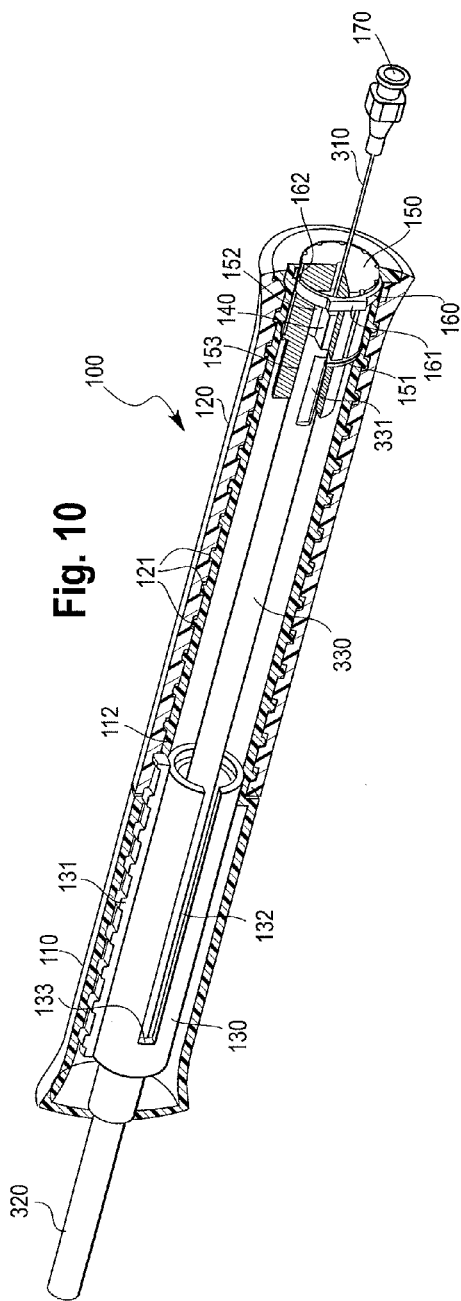
FIG. 10 is a partial sectional view of the prosthesis delivery device of FIG. 1.

A delivery device may be initially flushed with saline through the flush port 170. A guide wire may then be introduced into the device though the distal end, allowing the device to be introduced into a patient's vasculature and tracked to a desired location. FIG. 10 shows the deployment handle assembly 100 after the delivery device has been introduced into the patient's body and before any deployment steps have been performed. At this time, any safety latch 180 or other mechanism can be operated to "unlock" the handle assembly 100 to allow the handle assembly to be operated and a prosthesis deployment sequence to commence.

In operation, the physician places one hand on the first handle 110 and a second hand on the second handle 120. The physician slowly rotates the second handle 120 which causes the teeth 131 of the shuttle 130 to engage the threading 121 of the second handle 120 to move the shuttle 130 in a distal direction, thus unsheathing at least a proximal end of the prosthesis. The positioner 330 has sufficient rigidity/stiffness to resist buckling of the positioner 330 as the sheath 320 is withdrawn over it. As the shuttle 130 is further advanced distally over the positioner 330, the distal end of the shuttle 130 moves distally so that it is disposed over the proximal end of the rotary dial 150 as illustrated in FIG. 11. Continued rotation of the second handle 120 advances the shuttle 130 and the rotary dial 150 in a distal direction until the rotary dial threading 151 encounters or abuts the proximal end of the collar 160, at which time the user will sense resistance such that the second handle 120 can no longer be rotated and the distal end of the rotary dial 150 protrudes from the distal end of the first handle 110. The distal movement of the rotary dial 150 shifts the rotary cog 140 from the distal end of the rotary dial 150 to proximal end 153 of the rotary dial 150.

The rotary dial 150 may then be manually rotated by the physician to release the proximal end of the prosthesis. The proximal end 153 of the rotary dial 150 is disposed about the rotary cog 140 such that rotation of the rotary dial 150 causes the rotary cog 140 and the attached cannula 310 to rotate. As the rotary dial 150 is rotated, the inside threads 163 of the collar 160 engages the threading 151 on the rotary dial 150. The respective threads 163, 151 are configured to allow a selected number of rotations of the rotary dial. Preferably, the number of rotations permitted by the respective threading 163, 151 is the number of rotations required to release the proximal end of the prosthesis. Until the rotary dial 150 is rotated to release the proximal end of the prosthesis, the physician cannot further rotate the second handle 120 to withdraw the shuttle 130 (and the attached sheath 320) further to release the distal end of the prosthesis.

As illustrated in FIG. 13, the second handle 120 can then be further rotated to continue withdrawing the shuttle 130 distally from the first handle 110 and to retract the sheath 320 in a distal direction. As the second handle 120 is further rotated, it also moves the rotary dial 150 in a distal direction. The shuttle 130 is prevented from being entirely withdrawn from the first handle 110 by the proximal end 133 of the shuttle slot 132 which engages the tab 111 of the first handle 110. FIGS. 22-23 show the release of the prosthesis as the second handle 120 is further rotated. The rotation of the second handle 120 exposes the distal end of the prosthesis. The simultaneous withdrawal of the rotary dial 150 withdraws the trigger wire 790 from the distal end of the prosthesis, which then releases the prosthesis in the body at the location of the deployment site.

Figure 15:
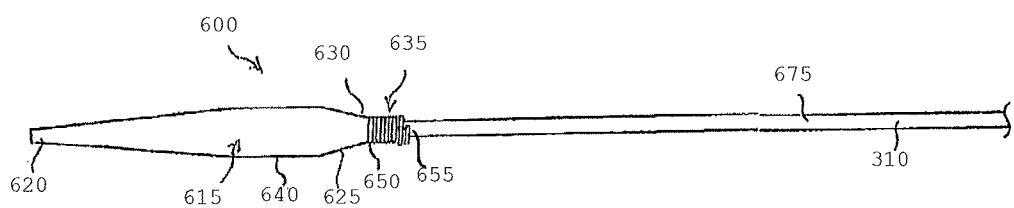
FIG. 15 is a partial side view of a proximal end of a prosthesis delivery device of FIGS. 1 and 2 with an exemplary prosthesis proximal stent attachment and release mechanism.
Figure 16:
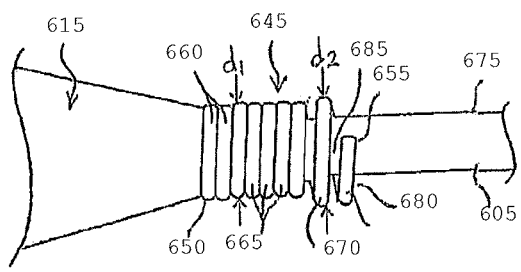
FIG. 16 is an enlarged partial side view of the proximal stent attachment and release mechanism of FIG. 15.

FIGS. 15 and 16 illustrate a proximal portion of the delivery device 600, and in particular, one example of an attachment and release mechanism for the proximal end of a prosthesis that can be operated using the delivery handle assemblies 100, 200 described above. FIG. 15 shows a tapered nose cone 615 having a proximal tip 620 at the proximal end of the inner cannula 310. Nose cone 615 has a reverse distal taper 625 at its distal end 630. The nose cone surface 640 presents a smooth tapered surface to facilitate entry into and movement through a body vessel. An exemplary attachment and release mechanism 635 is disposed at or near the distal end 630 of the nose cone 615 and on the inner cannula 310. As shown in enlarged view in FIG. 16, the attachment and release mechanism 635 comprises coiled member 645 having a proximal end 650, a distal end 655, and a plurality of turns 660 disposed there between.

In one non-limiting example, the proximal end 650 of the coiled member 645 is secured to the outer surface 675 of the cannula 310 using a suitable attachment mechanism, such as a solder, weld, mechanical attachment, friction fit, crimp, or combination of these or other techniques. Accordingly, the proximal end 650 of the coiled member 645 cannot move relative to the outer surface 675 of the inner cannula 310. The proximal end 650 of the coiled member 645 comprises a first diameter d 1, which may be approximately the same diameter, or slightly greater than, an outer diameter of the cannula 310.

The distal end 655 of the coiled member 645 is unsecured relative to the outer surface 675 of the inner cannula 310, as shown in FIG. 16. The distal end 655 of the coiled member 645 may comprise a second diameter d 2 which is greater than the first diameter d 1 of the proximal end 650 of the coiled member 645. There is a separation or gap 680 between the distal end 655 of the coiled member 645 and the outer surface 675 of the cannula 310, as best seen in FIG. 16.

The plurality of turns 660 are divided into a proximal series of turns 665, which have the first diameter d 1, and a distal series of turns 670, which have the second diameter d 2. The proximal series of turns 665 may be disposed in close proximity or abutting one another, as depicted in FIG. 16. By contrast, the distal series of turns 670 may be spaced apart from one another a greater distance than the proximal series of turns 665. In FIG. 16, the distal series of turns 670 are spaced apart a predetermined distance denoted by spacing 685.

Figure 17:
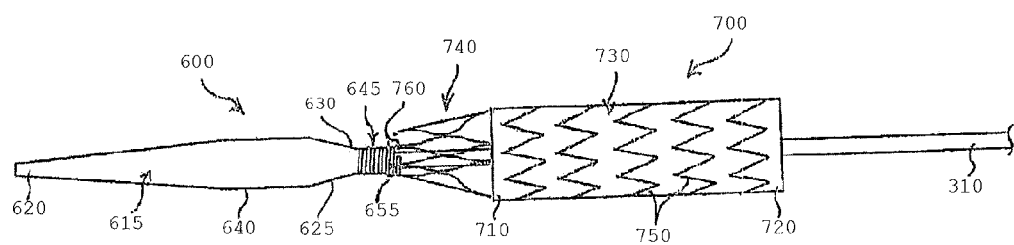
FIG. 17 is a partial side view of a delivery device having a prosthesis carried on the proximal end thereof with a proximal stent attached to the attachment and release mechanism.
Figure 18:
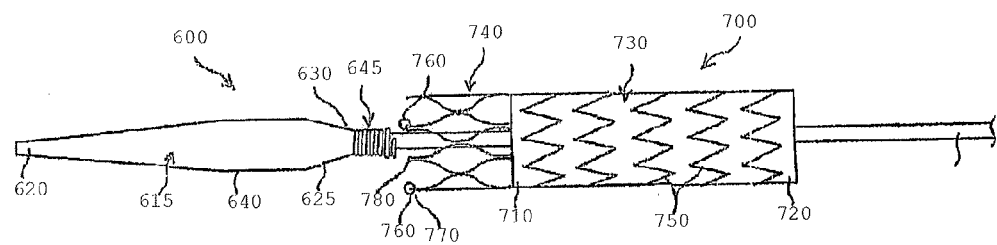
FIG. 18 illustrates the delivery device of FIG. 17 with the proximal stent released from the attachment and release mechanism.

As shown in FIGS. 17 and 18, prosthesis, such as stent graft 700, is disposed on the device and has a proximal end 710 and distal end 720. Stent graft 700 includes, in this example, a graft material 706, a bare proximal top stent 740 (though the disclosure is not so limited), and one or more stents 750 attached to the graft material 730. The stents 750 may be on either or both inner and outer surfaces of the tube of graft material 730 and may have the characteristics of self-expanding stents, balloon expanding stents, or both, depending on the desired stent characteristics.

As shown in FIGS. 17 and 18, the stent graft 700 has an uncoupled state in which the stent graft 700 is positioned coaxially over the inner cannula 310 with the proximal end 710 of the stent graft 700 in longitudinal proximity relative to the distal end of the coiled member 645, as shown in FIG. 18. During assembly, one or more loops 760 that are coupled to the proximal apices 770 of the stent 740 are threaded around the distal end of the coiled member 645 one at a time, preferably until all of the loops 760 are coupled to the coiled member 645. Such coupling may be achieved by rotating the inner cannula 310 in a clockwise direction until the proximal end 710 of the stent 740 is sufficiently compressed in a radially inward direction, as depicted in FIG. 17. A gap 680 between the distal end of the coiled member 645 and the outer surface of the inner cannula 310 permits positioning of the loops 760 in the series of turns at the distal end of the coiled member 645. This type of attachment system of the proximal stent to the delivery system is more fully described with reference to FIGS. 4 and 5 of U.S. application Ser. No. 13/796,395 (filed Mar. 12, 2013) which description and figures, and in particular FIGS. 1, 2, 4 and 5, are hereby incorporated by reference in their entirety.

The loops 760 are further accommodated within a spacing between the distal series of turns. The loops 760 preferably are coupled to the coiled member 645 in a manner in which at least one loop 760 is positioned around at least one full turn of the distal series of turns, and preferably around at least 1.5 turns at the distal end 655 of the coiled member 645, thereby reducing the likelihood of inadvertent uncoupling of the loops 760 from the coiled member 645.

The coupling shown in FIG. 16 secures the stent 740 to the cannula 310 via the coiled member 645 in a manner that may subsequently facilitate insertion of the subassembly comprising the inner cannula 310 and the stent graft 700 into an outer sheath, such as sheath 320 described above. As will be apparent, the outer sheath 320 is configured to radially restrain other regions of the stent graft 700 for delivery to a target site within a patient's anatomy.

The loops 760 may be coupled to every other proximal apex 770 as shown in FIG. 17 to restrain the stent 740 during delivery. In such a case, the loops 760 are not coupled to the second proximal apices 780, which may comprise barbs. By restraining the alternating proximal apices 770 using the loops 760 coupled to the coiled member 645, the adjacent second proximal apices 780 also may be indirectly pulled in a radially inward direction during delivery. The configuration of the stent 740 facilitates the indirect compression of the adjacent second proximal apices 780. Since only selected ones of the proximal apices are restrained during delivery, the number of loops 760 may be reduced. This type of attachment system of the proximal stent to the delivery system is more fully described with reference to FIGS. 4 and 5 of U.S. application Ser. No. 13/796,395 (filed Mar. 12, 2013) which description and figures, and in particular FIGS. 1, 2, 4 and 5, are hereby incorporated by reference in their entirety.

Figure 19:
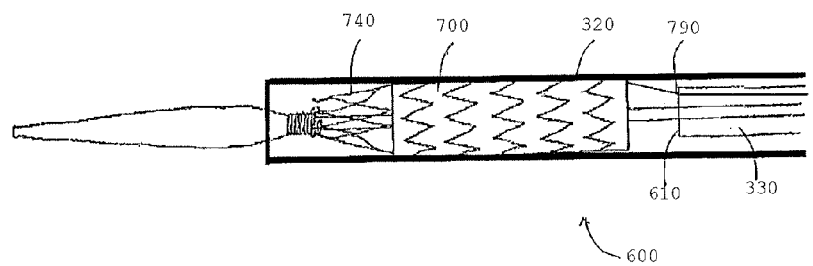
FIGS. 19-23 illustrate one example of a method for releasing a prosthesis from a delivery device.
Figure 21:
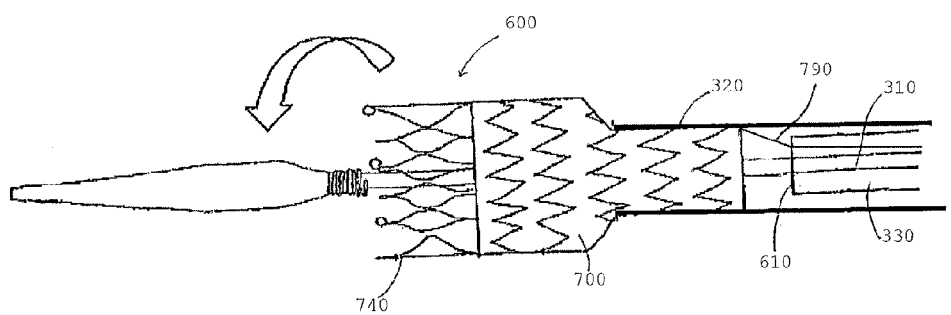

FIGS. 19-23 illustrate the controlled and sequential release of the stent graft from the delivery device using the handle assemblies 100, 200 described herein. More particularly, FIG. 19 shows the stent graft 700 loaded on the delivery device and compressed by the sheath 320. In operation, the operator withdraws the sheath 320 in the direction indicated by the arrow shown in FIG. 20. This may be accomplished by pulling back on the second handle 210 of handle assembly 200 and/or by rotating second handle 120 of handle assembly 100 to move it in a distal direction, thus withdrawing the sheath 320. When the proximal stent 740 is at least partially exposed, and it is desirable to deploy the restrained proximal end of the stent 740, the inner cannula 310 may be rotated in a counter-clockwise direction (as shown by the arrow in FIG. 21) until the loops 760 are uncoupled from the coiled member 645, i.e., in a reverse manner from which the loops 760 were coupled to the coiled member 645. Rotation of the inner cannula 310 may be accomplished as described in detail above, such as by rotating rotary collar 225 of handle assembly 200 and/or rotating rotary dial 150 of handle assembly 100. The proximal stent 740 then may be deployed as shown in FIGS. 17, 18, and 21.

After deployment of the proximal stent 740 has been completed, the remainder of the stent graft 700 may be deployed by further actuation of the handle assembly 100 and/or 200. In particular, further retraction of the sheath 320 (as shown by the arrows in FIGS. 20, 22 and 23) and/or actuation of any other mechanisms (such as trigger wires) that are constraining the remainder of the stent graft 700 may now be initiated. FIGS. 22-23 illustrate the release of the distal end of the stent graft 700 by retracting the sheath 320 and releasing the trigger wire 790. In one non-limiting example, further retraction of the sheath and trigger wire release may be accomplished by further manipulating handle assembly 100 and/or 200, such as by moving the second handle 120, 210 further in a distal direction (whether by rotation of 120 or pulling back on 210.

Advantageously, the proximal end of the stent 740 is radially restrained without the use of conventional trigger wires that span a full longitudinal length of the delivery system. Accordingly, the radial profile of the delivery system may be reduced, thereby reducing packing density of the system. Moreover, deployment may be simplified as reduced deployment forces are expected to be needed relative to the use of conventional trigger wires. As a further advantage, deployment of a stent using the described device comprising at least one coiled member may allow for more precise positioning of the stent. In particular, deployment using the coiled member may provide a more controlled unwinding of the associated portion of the stent.

The invention claimed is:

1. A prosthesis delivery device comprising:
   a proximal end and a distal end;
   a rotatable inner cannula extending from the proximal end to the distal end;
   a prosthesis releasably coupled to the proximal end of the inner cannula;
   a sheath coaxial with the inner cannula, the sheath extending at least partially between the proximal and distal ends;
   a delivery handle assembly at the distal end of the delivery device, the delivery handle assembly comprising,
   a first handle disposed about the inner cannula,
   a rotary dial rotatably disposed about a distal end of the first handle;
   a second handle disposed about at least a portion of the distal end of the first handle, wherein the second handle is longitudinally moveable relative to the first handle between a first position and a second position, wherein when the second handle is in the first position the sheath is coaxially disposed about the prosthesis and rotation of the rotary dial is prevented, and when the second handle is in the second position the sheath is retracted distally to expose at least a portion of the prosthesis and rotation of the dial is permitted.

2. The prosthesis delivery device of claim 1 wherein the second handle slides distally from the first position to the second position.

3. The prosthesis delivery device of claim 1 wherein the second handle is axially rotated distally to move the second handle from the first position to the second position.

4. The prosthesis delivery device of claim 1 wherein the rotary dial is covered by the second handle when the second handle is in the first position and the rotary dial is exposed when the second handle is in the second position.

5. The prosthesis delivery device of claim 1 wherein the prosthesis comprises a stent graft having a stent at the proximal end of the stent graft and wherein the stent comprises a series of proximal apices.

6. The prosthesis delivery device of claim 5 wherein the proximal end of the inner cannula comprises a coil that releasably engages one or more of the stent proximal apices.

7. The prosthesis delivery device of claim 1 wherein rotation of the rotary dial imparts rotation to the inner cannula to thereby release a proximal end of the prosthesis from the inner cannula.

8. The prosthesis delivery device of claim 1 further comprising at least one trigger wire, wherein a proximal end of the trigger wire is releasably engaged with a distal end of the prosthesis and a distal end of the trigger wire is secured to the handle assembly.

9. The prosthesis delivery device of claim 8 wherein the second handle is further distally moveable from the second position to a third position and wherein movement of the handle to the third position retracts the trigger wire and releases the distal end of the prosthesis from the inner cannula.

10. The prosthesis delivery device as claimed in claim 1, wherein the handle assembly further comprises a safety mechanism configured to prevent the inadvertent movement of the second handle.

11. The prosthesis delivery device of claim 1 further comprising a rotary gear system disposed within the rotary dial and wherein the rotary gear system is configured to impart rotation to the inner cannula when the rotary dial is rotated.

12. The prosthesis delivery device of claim 11 wherein the gear system comprises a first gear and second gear, the second gear being secured to the rotatable inner cannula, and wherein rotation of the rotary dial imparts rotation to the first gear and the first gear imparts rotation to the second gear to thereby rotate the inner cannula.

13. The prosthesis delivery device of claim 12 wherein the rotary dial and the first gear have a 1:3 gearing ratio.

14. A method for sequentially releasing a prosthesis from a delivery device, the delivery device comprising a rotatable inner cannula extending from a proximal end to a distal end; a prosthesis releasably coupled to the proximal end of the inner cannula; a sheath coaxially disposed about at least a portion of the prosthesis; a delivery handle assembly at a distal end of the delivery device, the delivery handle assembly comprising, a first handle disposed about the inner cannula, wherein the first handle comprises a rotary dial rotatably disposed about a distal end of the first handle; a second handle disposed about at least a portion of the distal end of the first handle, the method comprising:
- actuating the second handle from a first position to a second position to retract the sheath to expose at least a portion of the prosthesis;
- rotating the rotary dial to release the proximal end of the prosthesis;
- actuating the second handle from the second position to a third position to release a distal end of the prosthesis.

15. The method of claim 14 wherein the prosthesis comprises a stent graft having a stent at the proximal end thereof and wherein the proximal end of the inner cannula comprises a coil that is releasably engaged with one or more proximal apices of the stent.

16. The method of claim 15 wherein rotation of the rotary dial imparts rotation to the inner cannula to release the coil at the proximal end of the inner cannula from the proximal stent apices.

* * * * *